US00PP34841P2

(12) United States Plant Patent
Alcock

(10) Patent No.: US PP34,841 P2
(45) Date of Patent: Dec. 13, 2022

(54) ***CORDYLINE* PLANT NAMED 'ALCORLIPA'**

(50) Latin Name: *Cordyline australis*
Varietal Denomination: ALCORLIPA

(71) Applicant: Neil Alcock, Gwynedd (GB)

(72) Inventor: Neil Alcock, Gwynedd (GB)

( * ) Notice: Subject to any disclaimer, the term of this patent is extended or adjusted under 35 U.S.C. 154(b) by 0 days.

(21) Appl. No.: 17/707,145

(22) Filed: Mar. 29, 2022

(30) Foreign Application Priority Data

Mar. 14, 2022 (QZ) ..... PBR 20220684

(51) Int. Cl.
*A01H 5/12* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/12
See application file for complete search history.

(56) References Cited

PUBLICATIONS https://ne-np.facebook.com/commerce/listing/2214154458766287/?media_id=1&ref=share_attachment; May 16, 2022; 1 page.*

* cited by examiner

*Primary Examiner* — Kent L Bell
(74) *Attorney, Agent, or Firm* — Penny J. Aguirre

(57) ABSTRACT

A new cultivar of *Cordyline australis* plant named 'ALCORLIPA' that is characterized by its variegated foliage with centers that are lime-green in color and margins that are creamy white in color, its compact plant habit, and its slender leaves that are linear in shape.

2 Drawing Sheets

Botanical classification: *Cordyline australis.*
Cultivar designation: 'ALCORLIPA'.

CROSS-REFERENCE TO A RELATED APPLICATION

This application claims priority to European Community Plant Variety Office (CPVO) Plant Breeder's Rights Application No. 2022/0684 filed on Mar. 14, 2022, the entire contents of which is incorporated by reference herein.

BACKGROUND OF THE INVENTION

The present invention relates to a new and distinct cultivar of *Cordyline australis* and will be referred to hereafter by its cultivar name, 'ALCORLIPA'. 'ALCORLIPA' represents a new cultivar of cabbage tree or cabbage palm and is grown as a foliage plant for landscape and container use.

The new cultivar was discovered as a naturally-occuring chimeral mutation by the Inventor in Gwynedd, United Kingdom in May of 2017 of *Cordyline australis* 'Torbay Dazzler' (not patented) that was growing in a production field.

Asexual propagation of the new cultivar was first accomplished by tissue culture using meristemac tissue by the Inventor in Gwynedd, United Kingdom in May of 2017. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'ALCORLIPA' as a new and unique cultivar of *Cordyline.*

1. 'ALCORLIPA' exhibits variegated foliage with centers that are lime-green in color and margins that are creamy white in color.
2. 'ALCORLIPA' exhibits a compact plant habit.
3. 'ALCORLIPA' exhibits slender leaves that are linear in shape.

The parent plant of 'ALCORLIPA', 'Torbay Dazzler', differs from 'ALCORLIPA' in having variegated foliage that is brown and cream in color. 'ALCORLIPA' can be compared to the *Cordyline* cultivars 'Jive' (U.S. Plant Pat. No. 25,123) and 'Albertii' (not patented). 'Jive' and 'Albertii' are both similar to 'ALCORLIPA' in having variegated and cascading foliage. 'Jive' differs from 'ALCORLIPA' in having variegated foliage with creamy-white to yellow centers and green margins. 'Albertii' differs from 'ALCORLIPA' in having variegated foliage with centers that are dark green in color with creamy white margins.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but is not limited to a website listing by Genesis Plant Marketing Ltd, Instagram (Neil Alcock), Pacific Plug and Liner, and Visions Pictures.

BRIEF DESCRIPTION OF THE DRAWINGS

The accompanying color photographs illustrate the overall appearance and distinct characteristics of the new *Cordyline*. The plants in the photographs were taken of a 1-year-old plant of 'ALCORLIPA' as grown in a 17-cm container in a greenhouse in Pontrug, Caernarfon, Gwynedd, The United Kingdom.

Figure 1:
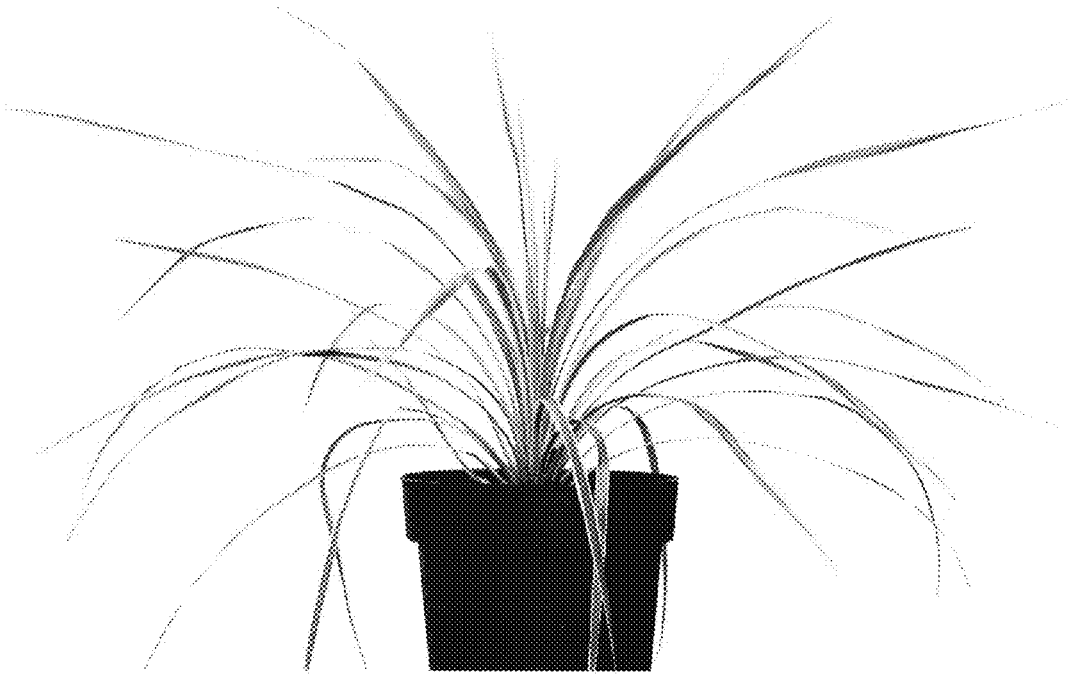
FIG. 1 provides a side view of a plant of 'ALCORLIPA'.
Figure 2:
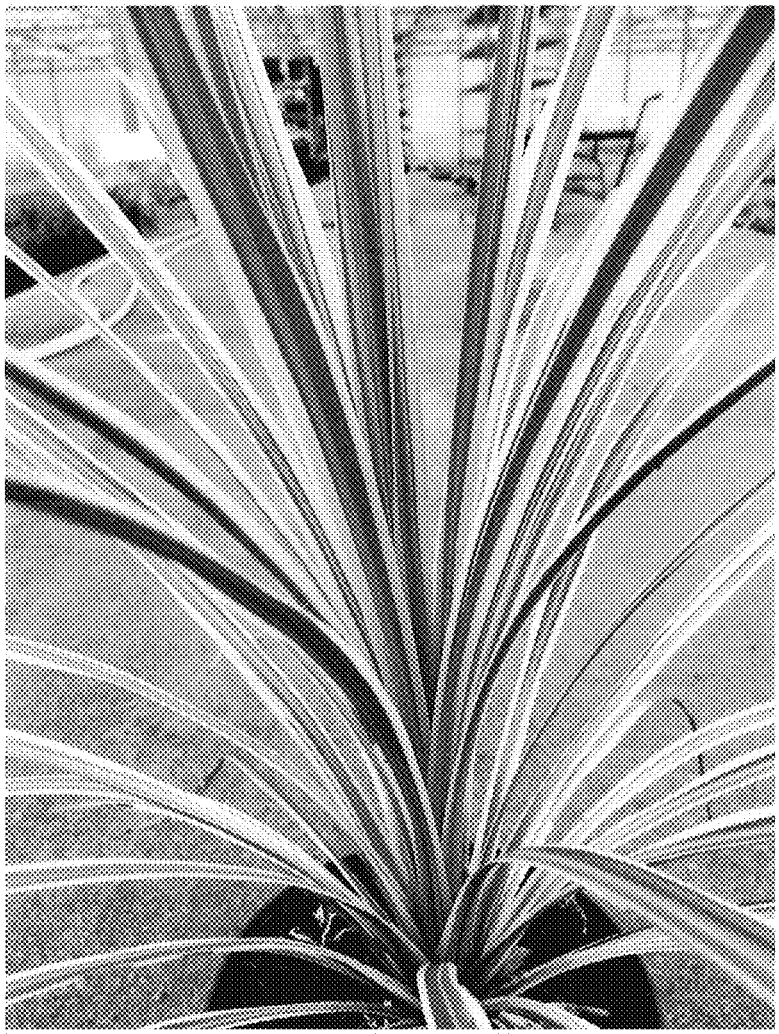
FIG. 2 provides a close-up view of the foliage of 'ALCORLIPA'.

The colors in the photographs are as close as possible with the photographic and printing technology utilized and color values cited in the detailed botanical description accurately describe the colors of the new *Cordyline*.

DETAILED BOTANICAL DESCRIPTION OF THE PLANT

The following is a detailed description of plants 1 year in age as grown in 17-cm containers in a greenhouse in Pontrug, Caernarfon, Gwynedd, The United Kingdom. The phenotype of the new cultivar may vary with variations in environmental, climatic, and cultural conditions, as it has not been tested under all possible environmental conditions. The color determinations are in accordance with The 2015 Colour Chart of The Royal Horticultural Society, London, England, except where general color terms of ordinary dictionary significance are used.

General description:

*Plant type*.—Perennial.

*Plant habit*.—Compact.

*Plant size*.—Average of 36.8 cm in height and 69.5 cm in spread as one-year-old plant.

*Blooming period*.—No flower production has been observed.

*Hardiness*.—At least in U.S.D.A. Zones 8b to 12.

*Diseases and pests*.—No susceptibility or resistance to diseases or pests has been observed.

*Environmental stresses*.—Drought and heat resistant.

*Root description*.—Fibrous.

*Propagation*.—Tissue culture.

*Growth rate*.—Moderate.

*Root development*.—10 weeks to produce a young plant from a rooted cutting, 52 weeks from propagation to a saleable plant.

Stem description: Main shoot grows from base, no stems present.

Foliage description:

*Leaf shape*.—Linear.

*Leaf division*.—Simple.

*Leaf quantity*.—38.

*Leaf base*.—Sheathing, sheath length; average of 1.2 cm in length, 1.5 cm in width, color; upper side 146A, base 157B, lower side 144C, base 157A.

*Leaf apex*.—Narrowly acute, slightly tapering at the tip.

*Leaf venation*.—Parallel, upper surface; a blend of NN137A, 191A, 4D, 5D, and 160D, lower surface 146A.

*Leaf margins*.—Entire, glabrous and smooth.

*Leaf arrangement*.—Alternate in a basal rosette.

*Leaf aspect*.—Held in an average angle of 80° to stem, moderately carinate and moderately arching downward, tips pointing downward in an average angle of −40°.

*Leaf surface*.—Upper surface slightly glossy to moderately glossy, lower surface matte to very slightly glossy.

*Leaf color*.—Young upper surface; between 147B and 191A, margined and irregularly axillary striped 150A and 150B, young lower surface; 147B, margined and irregularly axillary striped 150A and 150B, mature upper surface; NN137A and 191A, margined and irregularly axillary striped 4D, 5D, and 160D, mature lower surface; a blend of NN137A, NN137B, 147A, 189A and 191A, margined and irregularly axillary striped 4D, 5D, and 160D.

*Leaf size*.—Average of 45.6 cm in length and 1.2 cm in width.

*Petiole*.—None present.

Flower description: No flowers have been observed to date, grown as a foliage plant.

It is claimed:

1. A new and distinct cultivar of *Cordyline* plant named 'ALCORLIPA' as herein illustrated and described.

* * * * *